US005814598A

United States Patent [19]

Fehr et al.

[11] Patent Number: 5,814,598

[45] Date of Patent: Sep. 29, 1998

[54] USE OF UNSATURATED ALIPHATIC ESTERS IN PERFUMERY

[75] Inventors: Charles Fehr, Versoix; José Galindo, Les Avanchets, both of Switzerland

[73] Assignee: Firmenich SA, Geneva, Switzerland

[21] Appl. No.: 936,196

[22] Filed: Sep. 23, 1997

[30] Foreign Application Priority Data

Oct. 23, 1996 [CH] Switzerland ............................ 2589/96

[51] Int. Cl.[6] ........................................ A61K 7/46

[52] U.S. Cl. ........................................ 512/26

[58] Field of Search ........................................ 512/26

[56] References Cited

U.S. PATENT DOCUMENTS

| | | | |
|---|---|---|---|
| 3,953,377 | 4/1976 | Naf | 512/26 |
| 4,000,327 | 12/1976 | Tseng et al. | 512/26 |
| 4,094,823 | 6/1978 | Hall et al. | 512/26 |
| 4,126,585 | 11/1978 | Conrad et al. | 512/26 |
| 4,267,075 | 5/1981 | Schaper et al. | 512/26 |
| 4,385,185 | 5/1983 | Gebauer et al. | 512/26 |
| 4,387,047 | 6/1983 | Sundt et al. | 252/522 |

OTHER PUBLICATIONS

K. Rinehart et al., Synthesis of 3–Dienoyl Tetramic Acids Related to Streptolydigin and Tirandamycin, *J. Am. Chem. Soc.,* 100:13 (1978), pp. 4229–4234.

O. Miyata et al., A Facile Conversion of (Z)–2–Alkenoic Esters into the (E)–Isomers with Diphenyl Disulfide, *Synthesis* (1990), pp. 1123–1125.

*Primary Examiner*—James H. Reamer

*Attorney, Agent, or Firm*—Pennie & Edmonds LLP

[57] ABSTRACT

The compounds of formula

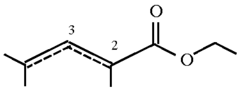

(I)

having a double bond in one of the positions indicated by the dotted lines, are useful as perfuming ingredients for the preparation of perfuming compositions and perfumed articles, to which they impart a refreshing and natural chamomile-like character.

6 Claims, No Drawings

USE OF UNSATURATED ALIPHATIC ESTERS IN PERFUMERY

Brief Description of the Invention

The present invention relates to the perfume industry. It relates more particularly perfuming compositions and perfumed products containing as a perfuming ingredient a compound of formula

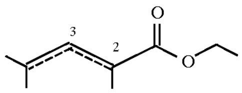

(I)

having a double bond in one of the positions indicated by the dotted lines.

The invention further provides a method to impart, improve, enhance or modify the odor properties of a perfuming composition or a perfumed product, which method comprises adding to said composition or product a compound of formula (I).

Another object of the invention is a perfuming composition or a perfumed product containing as active ingredient a compound of formula (I).

Prior Art

The structure of the compounds of formula (I) is known from the prior art. For example, ethyl 2,4-dimethyl-2pentenoate and its cis and trans configuration isomers have been described in the literature, namely in the context of organic syntheses (see for example V. J. Lee, A. R. Branfman, T. R. Herrin, and K.L. Rinehart, JACS, vol.100, 1978, 4229 —4234 or yet 0. Miyata, T. Shinada, I. Ninomiya, T. Naito, Synthesis, 1990, 1123-1124). However, we have been unable to find any mention of potentially useful odor properties for these compounds.

In fact, to our knowledge, no prior art document has ever suggested using as perfuming ingredients the unsaturated aliphatic esters of formula (I) for perfuming current consumer products and for the preparation of perfumes and perfuming bases.

Yet, we have now discovered that the compounds mentioned above possess very useful odor properties and that, as a result, they can be used for the preparation of perfuming compositions or perfumed products of varied nature.

Description of the Invention

The invention thus relates to the use of compounds (I) as perfuming ingredients and to the perfuming compositions and perfumed products which contain these compounds.

We have in fact ascertained that the compounds of formula (I) are able to impart to the compositions and consumer products into which they are incorporated a fresh and pleasant fragrance.

We have further discovered that the unsaturated aliphatic esters according to the invention possess distinct odor qualities and, namely, that ethyl 2,4-dimethyl-2-pentenoate develops a marked floral-chamomile odor note, having a slight tagetes type character, whereas ethyl 2,4-dimethyl-3-pentenoate presents a fruity, slightly chamomile-like, aniseed-fennel, accompanied of a honey type undernote and of a pleasant and particularly fresh headnote reminiscent of the odor of apple.

Curiously, ethyl 2,4-dimethyl-2pentenoate and its (E) and (Z) configuration isomers possess distinct odor notes, the two isomers developing very useful odors wherein the chamomile type headnote is very powerful and is accompanied of a natural fruity character.

Thus, (E)-ethyl 2,4-dimethyl-2pentenoate turns out to be a choice perfuming ingredient, its odor possessing a fruity, herbaceous character, with a strong Roman chamomile connotation, as well as a honey type undernote which recalls the characteristic odor of phenylacetic acid. This pleasant fruity, chamomile odor note is very distinctive and natural, reminiscent of the odor of the angelic acid's esters, without however the fat, butyric character of the latter.

Furthermore, although its chamomile note is reminiscent of that of the chamomile type esters known heretofore, (E)-ethyl 2,4-dimethyl-2-pentenoate possesses a far more natural and powerful odor than the latter known compounds. We observed in fact that, when compared to the latter in a synthetic chamomile oil, it was able to impart a distinctly richer, more sophisticated fragrance than Methylchamomile (butyl 2-methyl-pentanoate; origin: Givaudan-Roure, Vernier, Switzerland), with a more natural and elegant fruity character than angelic acid ester, and an enhanced fruity-chamomile quality compared to isopropyl methylbutyrate.

As to (Z)-ethyl 2,4-dimethyl-2pentenoate, it is also a useful perfuming ingredient, which develops a fruity, chamomile fragrance of pleasant and fresh character, very natural and just as elegant as that of the (E) isomer.

Moreover, it has also been ascertained that the mixtures of these two isomers, whatever the relative proportions of the two components, also reveal themselves as useful perfuming ingredients. In particular, the mixtures wherein the (E) isomer is present in a predominant amount are preferred perfuming ingredients according to the invention, possessing the odor characters which are typical this compound.

As a result of its odor qualities, (E)-ethyl 2,4-dimethyl-2-pentenoate is convenient for use in perfumery in a wide variety of compositions. For example, it can be of an advantageous employment in a floral composition, where it develops a far more powerful and fruitier, also more sophisticated, chamomile fragrance than namely 1,3-dimethyl-3-butenyl-isobutyrate (see for example, US 4 '387 '047), thus imparting to the perfume a novel odor effect.

Therefore, the odor properties of the compounds of formula (I) render them advantageous for both fine and functional perfumery applications. In a great variety of uses, any of the esters of the invention may reveal itself advantageous, on its own or admixed with currently used perfuming co ingredients. Amongst the products which can be perfumed by means of compounds (I) there can be cited perfumes and colognes, soaps, bath and shower gels, shampoos and other hair-care products, cosmetic preparations, ambient air deodorants, body deodorants, detergents and fabric softeners, or yet household products and all-purpose cleaners.

The proportions in which these compounds can be incorporated in the above-mentioned varied products vary in a wide range of values. Such values depend on the nature of the product to be perfumed and on the desired fragrance effect, and they are a function of the nature of any co-ingredients present in a given composition whenever compounds (I) are used in admixture with current perfuming ingredients, solvents or adjuvants.

By way of example, one can cite concentrations of the order of 1 to 5%, or even 10% or more by weight of compound of formula (I), relative to the weight of the perfuming composition into which it is incorporated. Lower concentrations than those mentioned above will be typically used when the same compounds are employed to perfume the variety of consumer products previously cited.

The term perfuming composition is meant to define here any mixture of perfuming ingredients selected amongst a variety of chemical classes comprising for instance alcohols, aldehydes, esters, ethers, ketones, ketals, nitriles, terpenic hydrocarbons, nitrogen- or sulfur-containing heterocyclic compounds, as well as natural or synthetic origin essential oils.

The compounds of the invention having a double bond in position 2 were prepared as mentioned before, following the synthesis described in the references cited above.

Ethyl 2,4-dimethyl-3-pentenoate was prepared as follows. A 25 ml flask equipped with a condenser and kept under nitrogen, was charged with 1.0 g (6.4 mmole) of ethyl 2,4-dimethyl-2-pentenoate and 0.975 g (6.4 mmole) of DBU (1,8-diazabicyclo[5.4.0]undec-7-ene), and the mixture was heated to 160° C. After 18 hours of reaction, followed by cooling, the reaction mixture was poured onto water and extracted with ether. The organic phase was washed successively with a 5% aqueous solution of HCI, water and brine, then dried on $Na_2SO_4$ and concentrated. After distillation on a bulb-to-bulb apparatus (80-100° C, 5.32 x 102 Pa) there were obtained 0,734 g of a 55:45 mixture of ethyl 2,4-dimethyl-2-pentenoate and ethyl 20 2,4-dimethyl-3-pentenoate. The two compounds were separated by flash-chromatography [$SiO_2$ (30 g), cyclohexane:ethyl acetate =98:2]. 0.180 g of ethyl 2,4-dimethyl-3-pentenoate were obtained. NMR(1H): 1,19(d, J=7, 3H); 1,25(t, J=7, 3H); 1,66(d, J=1, 3H); 1,72(d, J=1, 3H)

3,30(d, J=9; q, J=7, 1H); 4,12(q, J=7, 2H); 5,15(d, J=9; t, J=1, 1H) 6 ppm. NMR(13C): 175,6(s); 133,9(s); 124,0(d); 60,3(t); 39,1(d); 25,7(q); 18,1(q);

18,0(q); 14,2(q) 6 ppm. MS: 156($M^+$, 14), 141(4), 83(100), 67(10), 55(42).

The present invention will now be described in a more detailed manner by way of the following examples.

Preferred Embodiments of the Invention

Example 1

Preparation of a perfuming composition

A base perfuming composition was prepared by admixing the following ingredients:

| Ingredient | Parts by weight |
|---|---|
| Benzyl acetate | 170 |
| Cyclanol acetate | 20 |
| Verdyl acetate | 20 |
| Citronellol | 40 |
| 10% * Ethyl vanilline | 20 |
| Exaltex ® [1] | 140 |
| Heliotropine | 40 |
| Iralia ® [2] | 100 |
| Lilial ® [3] | 100 |
| Linalol | 120 |
| Phenethylol | 40 |
| Amyl salicylate | 40 |
| Benzyl salicylate | 120 |
| | 970 |

*in dipropyleneglycol
[1]pentadecanolide; origin: Firmenich SA, Geneva, Switzerland
[2]methyl-ionone; origin: Firmenich SA, Geneva, Switzerland
[3]2-methyl-3-(4-tert-buty1-1-phenyl)-propanal; origin: Givaudan-Roure, Vernier, Switzerland Upon adding to the herbaceous type base composition above-indicated 30 parts by weight of (E)-ethyl 2,4-dimethyl-2pentenoate there was obtained a novel composition possessing a particularly fruity headnote which was reminiscent of the odor of Roman chamomile, such that the ensemble had acquired a more lively and distinctly stronger and more elegant character.

Example 2

Preparation of a perfuming composition

A base perfuming composition having a powdery floral, woody connotation was prepared by admixture of the following ingredients:

| Ingredient | Parts by weight |
|---|---|
| Cyclanol acetate | 30 |
| Verdyl acetate | 80 |
| Anisic aldehyde | 30 |
| Dihydromyrcenol[1] | 30 |
| p-Tert-butyl-cyclohexyl acetate | 210 |
| Exaltex ® [2] | 150 |
| Isoraldeine ® [3] | 80 |
| Jasmal ® [4] | 80 |
| Amyl salicylate | 60 |
| Tonalid ® [5] | 60 |
| Vertofix coeur[6] | 80 |
| Violet essential oil | 80 |
| Total | 970 |

[1]2,6-dimethyl-7-octen-2-ol; origin: International Flavors & Fragrances, USA
[2]pentadecanolide; origin: Firmenich SA, Geneva, Switzerland
[3]origin: Givaudan-Roure, Vernier, Switzerland
[4]4-phenyl-1,3-dioxolane; origin: International Flavors & Fragrances, USA
[5](5,6,7,8-tetrahydro-3,5,5,6,8,8-hexamethyl-2-naphtyl)-1-ethanone; origin: PFW, Holland
[6]origin: International Flavors & Fragrances, USA Upon adding to this floral base composition 30 parts by weight of (E)-ethyl 2,4-dimethyl-2-pentenoate, it acquired a distinct fruity connotation, this compound having also imparted to the composition, in a far more marked manner, a pleasant fresh character.

Example 3

Preparation of a perfuming composition

A base perfuming composition with a fougere lavender-floral character was prepared by admixing the following ingredients:

| Ingredient | Parts by weight |
|---|---|
| Benzyl acetate | 45 |
| Linalyl acetate | 60 |
| Styrallyl acetate | 30 |
| Verdyl acetate | 80 |
| Aspic essential oil | 80 |
| Benzophenone | 60 |
| Coumarine | 30 |
| Cyclomethylene citronellol | 60 |
| Eugenol | 45 |
| Exaltex ® [1] | 30 |
| Lilial ® [2] | 45 |
| Linalol | 110 |
| Iralia ® [3] | 80 |
| Methylhexylketone | 45 |
| Methylnaphthylketone | 80 |
| Verdyl propanoate | 45 |
| Amyl salicylate | 45 |
| γ-Undecalactone | 15 |
| Total | 985 |

[1]pentadecanolide; origin: Firmenich SA, Geneva, Switzerland
[2]2-methyl-3-(4-tert-butyl-1-phenyl)-propanal; origin: Givaudan-Roure, Vernier, Switzerland
[3]methyl-ionone; origin: Firmenich SA, Geneva, Switzerland When 15 parts by weight of (E)-ethyl 2,4-dimethyl-2-pentenoate were added to this very classical fougere type base composition they imparted to it an enriching chamomile note, providing the new composition with a very modem, fresh and chamomile-like connotation.

What we claim is:

1. A perfuming composition or a perfumed product, containing as a perfuming ingredient a compound of formula

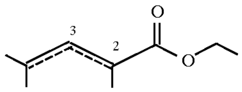

(I)

having a double bond in one of the positions indicated by the dotted lines.

2. A perfuming composition or a perfumed product according to claim 1, containing ethyl 2,4-dimethyl-2pentenoate or one of its isomers of (E) or (Z) configuration.

3. A perfumed product according to claim I or 2, in the form of a perfume or cologne, a soap, a bath or shower gel, a shampoo or other hair-care product, a cosmetic preparation, a body or ambient air deodorant, a detergent or a fabric softener, or a household product or all-purpose cleaner.

4. A method to impart, improve, enhance or modify the odor properties of a perfuming composition or perfumed product, which method comprises adding as a perfuming ingredient to said composition or product a compound of formula

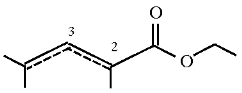

(I)

having a double bond in one of the positions indicated by the dotted lines.

5. A method according to claim 4, which comprises adding ethyl 2,4-dimethyl-2-pentenoate.

6. The method of claim 5, wherein ethyl 2,4-dimethyl-2-pentenoate is added in the form of one of its isomers of (Z) or (E) configuration.

* * * * *